United States Patent [19]

Daly et al.

[11] Patent Number: 5,755,747
[45] Date of Patent: May 26, 1998

[54] COCHLEAR IMPLANT SYSTEM WITH SOFT TURN ON ELECTRODES

[76] Inventors: Christopher Daly, 95 Beryl Crescent, Bilgoa Plateau, New South Wales 2107; Tony Mikeal Nygard, 14 Stacey Close, Kariong, New South Wales 2250; Paul Michael Carter, 9 Kerribee Place, Carlingford, New South Wales 2118; David Kerry Money, 50 Blackbutt Avenue, Pennant Hills, New South Wales 2120; James Finlay Patrick, 5 Arding Street, Lane Cove, New South Wales 2066; Christopher Mark Olufson, 431-33 Pearson Street, Gladesville, New South Wales 2066, all of Australia

[21] Appl. No.: 621,126

[22] Filed: Mar. 22, 1996

[30] Foreign Application Priority Data

Dec. 19, 1995 [WO] WIPO .................. PCT95/00864

[51] Int. Cl.$^6$ .................................................. A61N 1/14
[52] U.S. Cl. ............................................. 607/55; 607/63
[58] Field of Search ........................ 607/13, 55–57, 607/63, 64, 136, 137

[56] References Cited

U.S. PATENT DOCUMENTS

| | | | |
|---|---|---|---|
| 3,727,616 | 4/1973 | Lenzkes | 607/64 |
| 4,498,478 | 2/1985 | Bourgeois | 607/13 |
| 4,592,359 | 6/1986 | Galbraith | 607/63 |

FOREIGN PATENT DOCUMENTS 0247649 12/1987 Australia.

*Primary Examiner*—William E. Kamm
*Assistant Examiner*—George R. Evanisko
*Attorney, Agent, or Firm*—Gottlieb, Rackman & Reisman

[57] ABSTRACT

An implanted device such as a cochlear implant system includes a housing containing stimulating pulse generating circuitry, and a plurality of electrodes external of the housing and receiving the pulses. Between the pulses, parasitic voltages may build up between the electrodes. In order to control the inrush current due to these parasitic voltages, multi-position switches are provided which selectively couple the electrodes to resistors selected to dissipate the voltages at a preselected maximum current to protect the body organs.

9 Claims, 4 Drawing Sheets

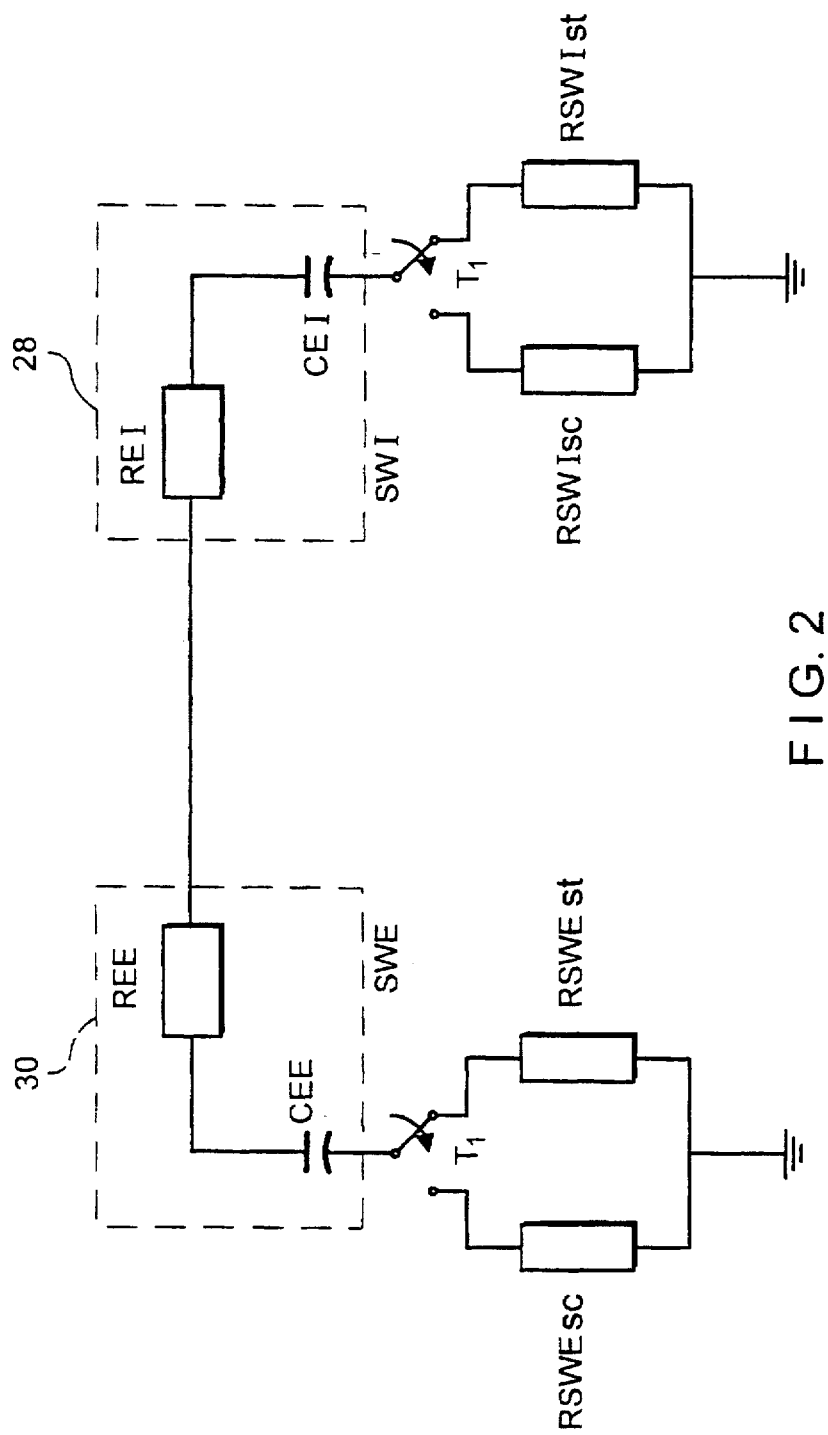
FIG. 2
FIG. 2A
FIG. 2B

5,755,747

COCHLEAR IMPLANT SYSTEM WITH SOFT TURN ON ELECTRODES

BACKGROUND OF THE INVENTION

A. Field of Invention

This invention pertains to cochlear implant systems using a plurality of electrodes to apply stimulation to a patient's auditory nerve to simulate ambient sounds, and more particularly to a system adapted to reduce inrush current through the electrodes when the electrodes are activated.

B. Description of the Prior Art

The subject invention pertains primarily to cochlear implant systems. These cochlear systems are used to provide therapy to a patient suffering from different illnesses. All of these systems require two sections: an internal or implanted section, and an external section. The external section includes a microphone for receiving ambient sounds and converting them to electrical signals. These electrical signals are processed and sent to the implanted section. The implanted section then generates excitation signals used to excite the auditory nerve of the patient between an intra-cochlear electrode array and one or more extra-cochlear electrodes. Prior to excitation, the electrodes are normally shorted to each other to equalize the electrode voltages.

A major disadvantage of these systems is as follows. When implanted, the extra-cochlear electrodes make contact with a different body fluid than the intra-cochlear electrodes. As a result, while they are idle, the electrodes tend to build up a potential difference which may range from 0 to 60 mV. Moreover during stimulation, a voltage of up to 300 mV may build up due to electro-chemical effects of the electrode tissue interface. This relatively high voltage may be maintained between the electrodes for several minutes after stimulation. As a result, when the electrodes are shorted, a relatively large inrush current can result between the electrodes. This large current inrush is undesirable because it can cause unwanted stimulation. In fact, the nerve can be sensitive to currents of about 10 microamps if sustained for a long enough period (typically a few milliseconds). Any current exceeding this threshold affects the auditory nerve and produces a response therein. As a result, the patient may be subjected to unwanted stimulation.

OBJECTIVES AND SUMMARY OF THE INVENTION

In view of the above-mentioned disadvantages of the prior art, it is an objective of the present invention to provide a cochlear implant system wherein the electrodes can be safely discharged prior to the application of a stimulating pulse.

A further objective is to provide a means of operating the electrodes of an implanted cochlear system without producing unwanted stimulation.

Yet a further objective is to provide a cochlear implant system incorporating the above-mentioned safety procedure without substantial increase in costs or complexity.

Other objectives and advantages shall become apparent from the following description. Briefly, in accordance with this invention, a cochlear implant system is provided with a switching network adapted to selectively short the electrodes together for charge balancing. Importantly, the switching means is provided with current limiting resistors which limit the current transients. Preferably a first resistor is provided for each switch for limiting the initial or inrush current and a second resistor which normally consists of the 'on' resistance of the switch connecting the electrode to the common return bus. The second resistor limits the current after the current has decayed substantially.

BRIEF DESCRIPTION OF THE DRAWINGS

FIG. 2 shows an electrical circuit with the electrode arrays and the body tissue therebetween shown as lumped elements;

FIG. 2A shows a first equivalent circuit for the soft turn-on period for the lumped circuit of FIG. 2;

FIG. 2B shows a second equivalent circuit for a short circuit period following the soft turn-on period;

DETAILED DESCRIPTION OF THE INVENTION

Figure 1:
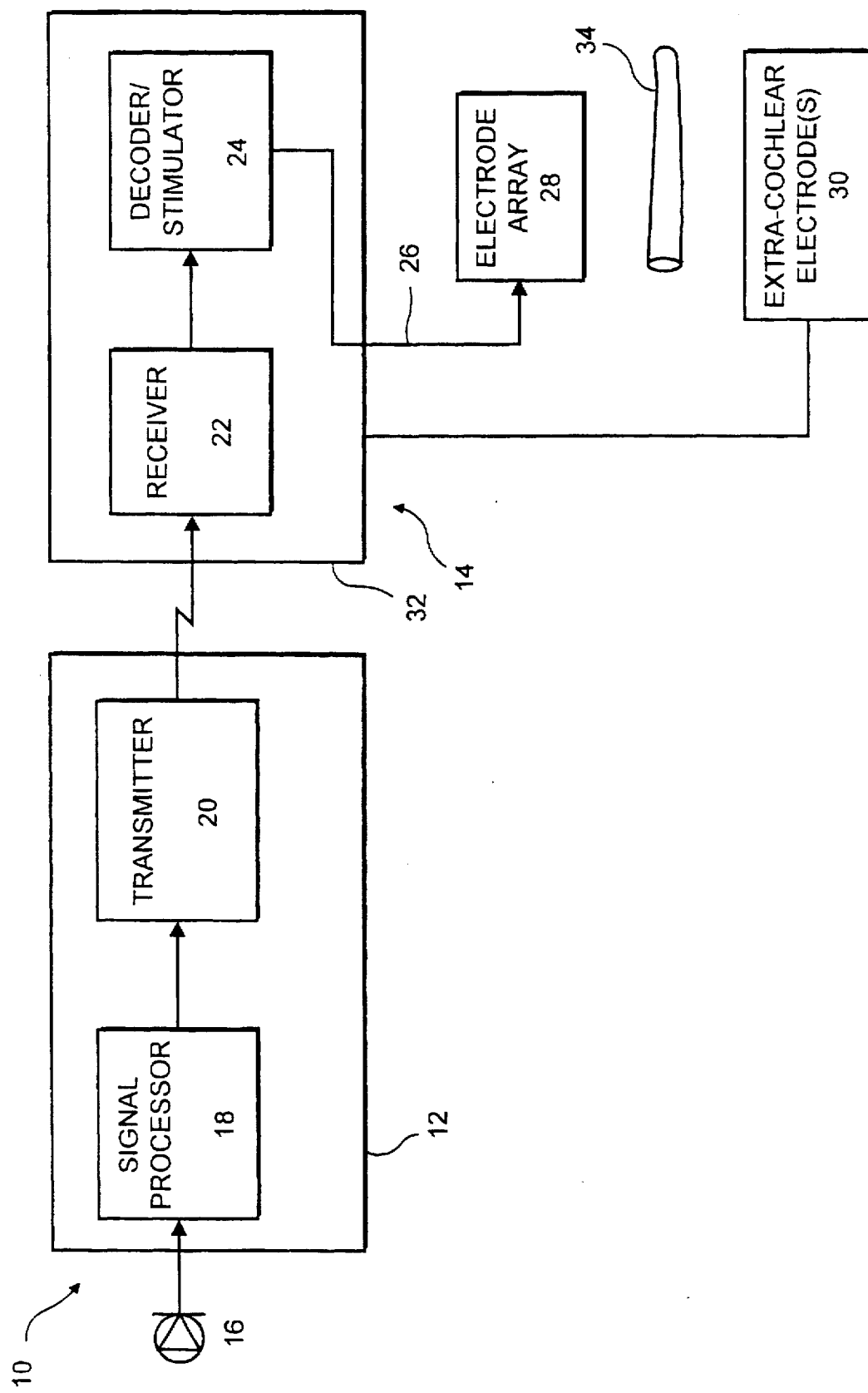
FIG. 1 shows a block diagram for a cochlear system constructed in accordance with this invention.

Referring now to FIG. 1, a cochlear system 10 constructed in accordance with this invention consists of an external portion 12, and an internal portion 14. The external portion 12 receives electrical signals from a microphone 16, which electrical signals correspond to ambient sounds. These signals are processed by a signal processor 18 and sent to a transmitter 20. The transmitter sends the signals from processor 12 to the implant section 14, using for example, inductive coupling.

In the implant portion 14, the signals are received by receiver 22. These signals are decoded and the appropriate stimulating signals generated. These stimulating signals are sent via a cable 26 to an electrode array 28 implanted into the patient's cochlea. One or more extra-cochlear return electrodes 30 may be provided for current to return to the implant section 14. In FIG. 1, the return electrodes 30 are shown as being separate from the implanted portion housing 32, however it should be understood the housing itself, or a portion of the housing may act as the return electrode. Typically, the electrode array 28 is immersed in the cochlear fluid so that the currents and electrical fields generated by its individual electrodes (not shown) stimulate the nerve 34.

As previously mentioned, a voltage may build up between electrodes 28 and 30 prior to the application of a stimulation. In accordance with the present invention, prior to the application of excitation to the electrode arrays, two successive periods are provided for discharging this electrode voltage. The first period is referred to as the soft turn-on (st) period and has a duration of T1 seconds. The second period is referred to as the short circuit (sc) period and has a duration T2. FIG. 2 shows an electrical circuit of the implant and the electrode arrays prior to the application of excitation signals. In this Figure all the electrodes of array 28 and the interfaces between the electrodes and the cochlea (including the cochlear fluid) are shown lumped into a resistor REI and a capacitor CEI. Similarly the extra-cochlear electrodes 30 and their interfaces are shown lumped as a resistor REE and a capacitor CEE. According to this invention, these lumped elements are connected in series with each other, as shown, and are also selectively grounded through resistors by respective switches SWE and SWI. During the soft turn-on period, switch SWI connects array 28 to a resistor RSWIst.

Similarly switch SWE connects array 30 to a resistor RSWEst. At the end of the soft turn-on period, to be determined as discussed below, switches SWI and SWE switch the respective arrays to corresponding resistors RSWIsc and RSWEsc, as shown. These resistors actually represent the internal resistances of the switches SWE and SWI, respectively, at different positions. A simplified equivalent circuit for the soft turn-on period is shown in FIG. 2A. The capacitance C in this circuit is given by the following:

$$C=CEE*CEI/(CEE+CEI).$$

The equivalent resistance RTst is the total series resistance of the circuit of FIG. 2 during the soft turn-on period and is given by:

$$RTst=REE+REI+RSWEst+RSWIst.$$

Initially, i.e. at t=0, the capacitor C is charged to a voltage VE. During the soft turn on period, the voltage across the capacitor C is $$Vst(t)=VE*exp(-t/Tst)$$

where Tst is the time constant of the circuit of FIG. 2A, i.e., $$Tst=RTst*C.$$

The current flowing through the circuit of FIG. 2A is given by $$Ist(t)=Vst(t)/RTst=(VE/RTst)*exp(-t/Tst).$$

Figure 3:
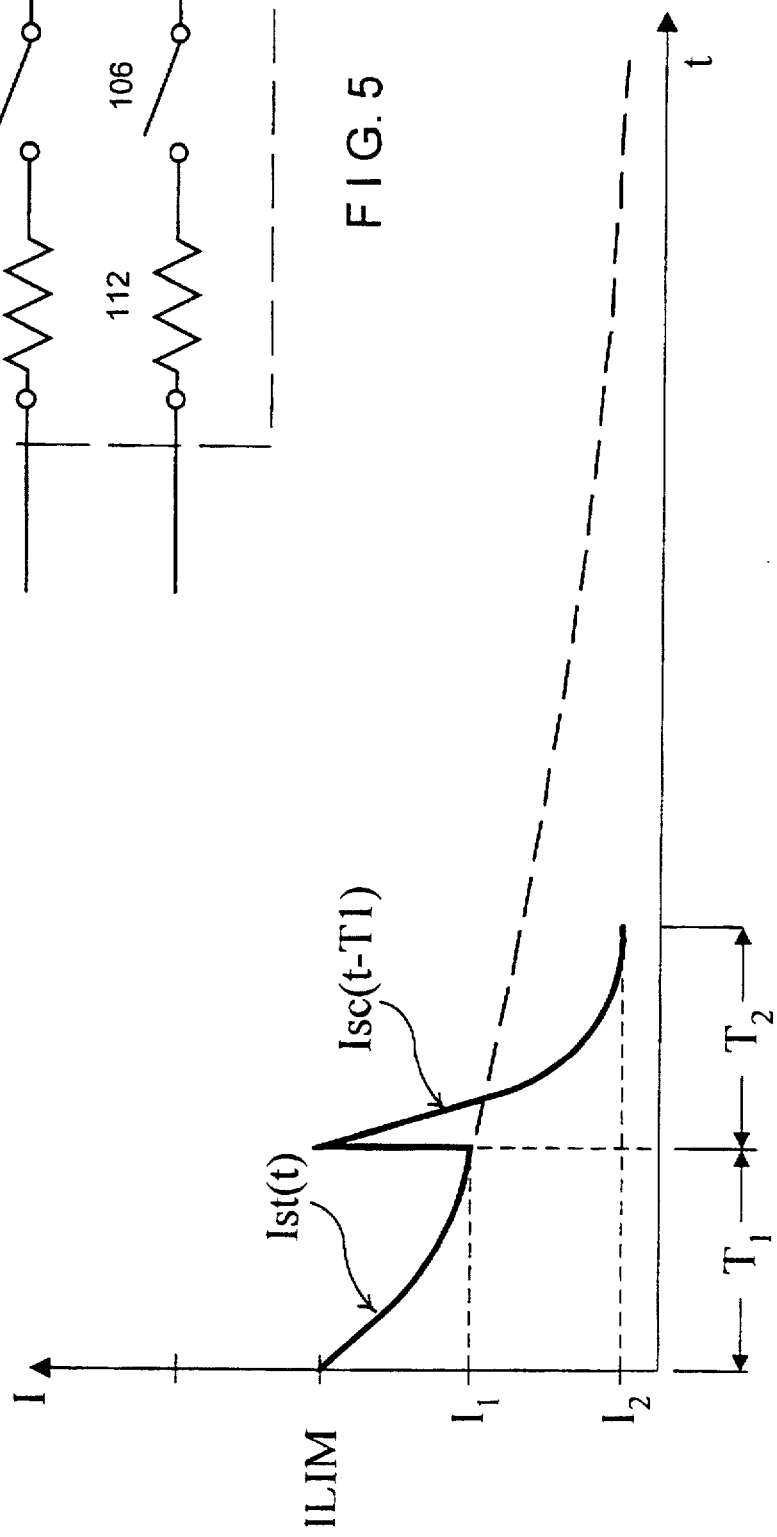
FIG. 3 shows the current flowing through the circuits of FIGS. 2A and 2B.

Current Ist(t) is illustrated in FIG. 3 and its maximum amplitude is VE/RTst. This current Ist(t) flows from one electrode array to the other and, as explained above, if its amplitude is large enough, it may be perceived by nerve 34. It has been found experimentally that in general nerve 34 is sensitive to currents exceeding 10 microamps. Therefore, in this invention, the maximum amplitude of the current flowing between the electrodes is limited to a threshold value ILIM which is preferably 10 microamps, although it may be lower as well.

Therefore in the above expression:

$$ILIM=VE/RTst=VE/(REE+REI+RSWEst+RSWIst)$$

The values of VE, REE and REI are determined experimentally.

The values of the switch resistances, RSWIst and RSWRst can then be determined from the above expression so that when the soft turn-on period starts the peak value of current Ist(t) decays to an adequately low level, as illustrated below.

More particularly, the combined switch on resistance RSW1 of all the switches used to energize the electrodes during a soft turn-on comprises the sum of the parallel resistance of all the soft turn-on resistors that are connected to the electrodes. Therefore, the total switch resistance during the soft turn-on RSWTst is given by:

$$RSWTst=RSWEst+RSWIst=(VE/ILIM)-REE-REI$$

FIG. 3 shows current Ist(t) as a function of time. From t=0 to t=T1, the current Ist(t) decays exponentially from ILIM until it reaches a value I1.

At the end of the turn on period, i.e., T1, the switches SWE, SWI connecting the electrode arrays are switched to a different, lower impedance state for a time which is referred to as the short circuit period (sc). The equivalent circuit for the short circuit period is shown in FIG. 2B. In this figure, the capacitor C is charged to a voltage equal to the voltage on capacitor C at the end of the soft turn-on period. Thus, the voltage on capacitor C during the second stage is given by:

$$Vsc(t')=VS*exp(-t'/Tsc)$$

where VS=Vst (T1)=VE exp (-T1/Tst)

and t'=t-T1. (i.e. the time from the beginning of the second period).

Similarly, the current during second period is given by:

$$Isc(t')=Vst(t')/RTsc$$

At the beginning of the short circuit period, the current Isc must not exceed the threshold ILIM. Therefore, $$Isc(t'=0)=ILIM=VS/RTsc$$

$$RTsc=VS/ILIM=(VE*exp(-T1/Tst))/ILIM$$

$$T1 \geq Tst*Ln(VE/(ILIM*RTsc))$$

(where Ln signifies the natural log).

Thus the above expression defines the minimum duration of the soft turn on stage T1. Alternatively, if the duration T1 is selected, then the total switch resistance RSWTsc must be:

$$RSWTsc>(RSWTst+REE+REI)*exp(-T1/Tst)-REE-REI$$

During the second period T2, the current IE decays exponentially to a value I2 at a faster time constant Tsc, as shown in FIG. 3.

Figure 4:
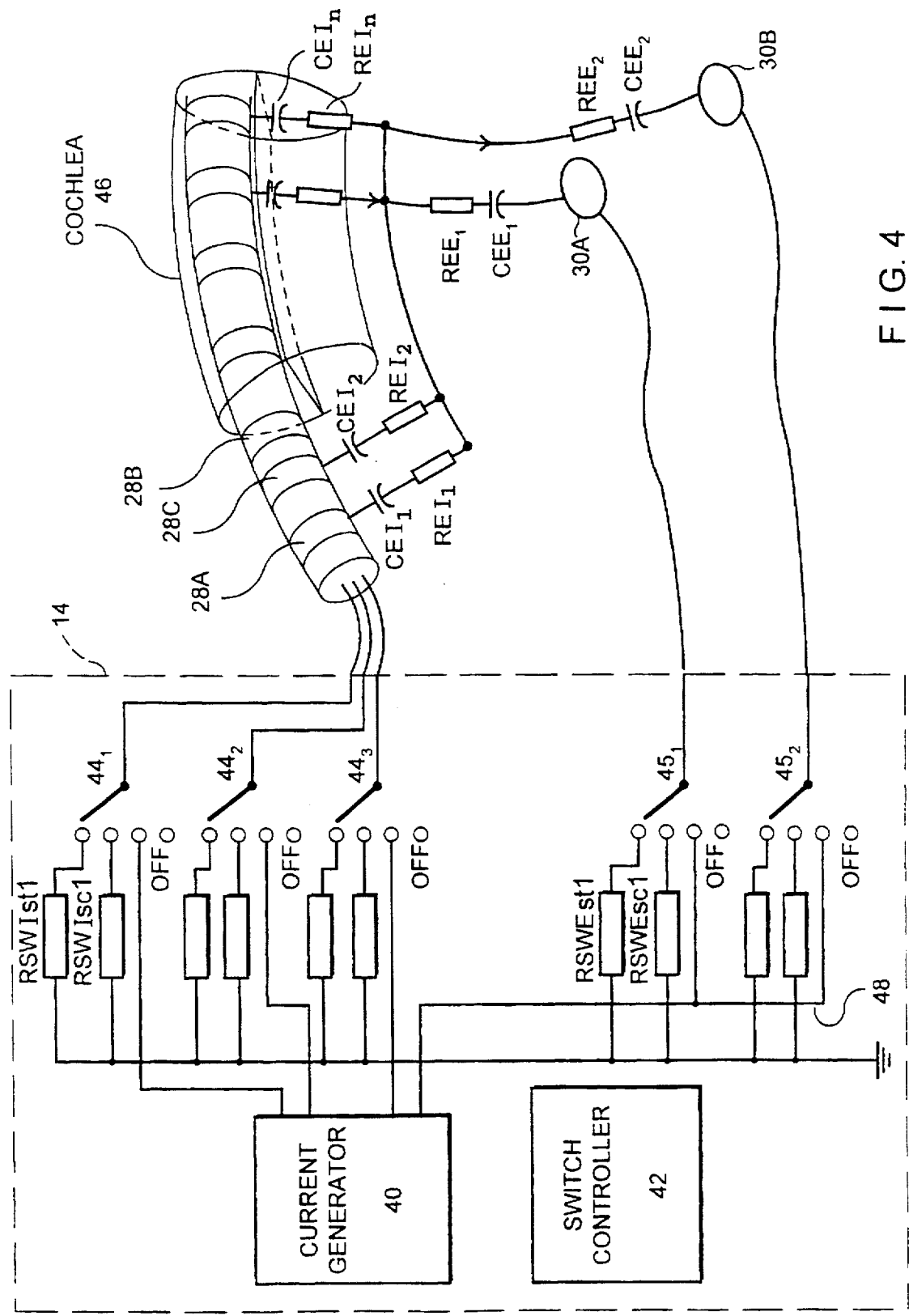
FIG. 4 shows a somewhat diagrammatic detail of the current limiting circuitry used in the invention.

A more detailed illustration of the invention is shown in FIG. 4. In this Figure implant section 14 includes a current generator 40, a switch controller 42 and two banks of switches 44, 45 controlled by switch controller 42. Each of the switches 44 are used to selectively control the current flow from one electrode in the intra-cochlear electrode array 28 disposed in cochlea 46 to any other electrode, including extra-cochlear electrodes 30. More particularly, each electrode of array 28, such as electrodes 28A, 28B, 28C is connected to a respective switch $44_1$, $44_2$, $44_3$. Similarly each extra-cochlear electrode 30A, 30B, is connected to a corresponding switch $45_1$, $45_2$. Each switch has four positions. In the first position shown in FIG. 4, each switch is connected to a high value resistor $RSWIst_i$, $RSWEst_i$, where i indicates the number of the switch. In the second position each switch is connected to a low value resistor $RSWI_{sci}$, $RSWE_{sci}$. In the third position, each switch is connected to the current generator 40. As seen in the FIG. 4, preferably each electrode of array 28 is individually connected to the current generator 40, while the extra-cochlear electrodes 30 are connected to the current generator by a common return bus 48. Finally, the fourth position of each switch 44, 45 is an OFF position. The resistors are also connected to a common ground bus 50 and correspond to resistor RSE and RSI in FIG. 2.

In addition, FIG. 4 shows the interface for each intra-cochlear electrode and the cochlear fluid and/or tissue as a capacitor $CEI_i$, in series with a resistor $REI_i$.

Similarly, the interface with each extra-cochlear electrode is represented as a capacitor $CEE_i$ in series with a resistor $REE_i$. These individual parameters corresponds to the lumped parameters discussed above as follows:

$$REE = \cfrac{1}{\cfrac{1}{REE_1} + \cfrac{1}{REE_2}}$$

$$REI = \cfrac{1}{\cfrac{1}{REI_1} + \cfrac{1}{REI_2} + \cdots \cfrac{1}{REI_n}}$$

$$CEE = \cfrac{1}{\cfrac{1}{CEE_1} + \cfrac{1}{CEE_2}}$$

$$CEI = \cfrac{1}{\cfrac{1}{CEI_1} + \cfrac{1}{CEI_2} + \cdots \cfrac{1}{CEI_n}}$$

$$RSWIst = \cfrac{1}{\cfrac{1}{RSWIst_1} + \cfrac{1}{RSWIst_2} + \cdots \cfrac{1}{RSWIst_n}}$$

$$RSWIsc = \cfrac{1}{\cfrac{1}{RSWIsc_1} + \cfrac{1}{RSWIsc_2} + \cdots \cfrac{1}{RSWIsc_n}}$$

$$RSWEst = \cfrac{1}{\cfrac{1}{RSWEst_1} + \cfrac{1}{RSWEst_2}}$$

$$RSWEsc = \cfrac{1}{\cfrac{1}{RSWEsc_1} + \cfrac{1}{RSWEsc_2}}$$

The invention operates as follows. When the device is powered down all the switches of banks 44, 45 are in the OFF position, allowing the electrodes 28, 30 to float. As a result, a potential charge may be built up on these electrodes. When the device becomes powered up, but prior to the application of stimulation currents, each electrode switch of banks 44, 45 is flipped to position one thereby connecting the electrodes 28, 30 to the ground bus 50 through the high value resistors $RSWEst_i$, $RSWIst_i$. As a result a current will flow from each intra-cochlear electrode 28 to at least one extra-cochlear electrode. In FIG. 4, currents 11, 12, 13 are shown as flowing from each electrode 28A, 28B, 28C to a extra-cochlear electrode 30A, 30B. It should be understood that in practice a much lower number of extra-cochlear electrodes 30 may be used than intra-cochlear electrodes. Moreover, some manufacturers may prefer to provide a single extra cochlear electrode 30, preferably disposed on or made an integral part of the casing 32.

The high value resistors RSWEst, RSWIst need not be identical but can be selected to limit the individual current flowing from each electrode 28. In addition, the total current I=i1+i2+i3 ... should also be limited so that at the time the switches are turned to the first positioned, the current I is limited to a maximum initial value ILIM. Thereafter the total current I decays exponentially at a time constant defined by the total resistance and interface capacitance of the electrodes, as shown during a first time period T1 in FIG. 3.

Typical values for the various parameters discussed are as follows:

CEE=20 uF
CEI=2.2 uF
REE=100 ohm
REI=91 ohm
ILIM=10 uA
VE=300 mV

Application of the previously developed equations generates the following values:

T1=200 msec
RSWTst=RSWIst+RSWEst=30,000 ohms
RSWTsc=RSWIsc+RSWEsc=890 ohms

If desired, a larger number of stages of voltage discharge, n, may be employed, instead of two. In this case, each electrode would be connected to the common bus through the resistors, each one having a smaller value than the previous one. There would be n such periods of discharge, T1 to Tn. During T1 the electrodes would be connected to the common bus by the highest value resistor, during T2 they would be connected through the next highest and so on.

In this fashion, the current flowing through the electrodes 28, 30 are effectively limited during the electrode grounding thereby insuring that the patient does not perceive unwanted stimulation.

Figure 5:
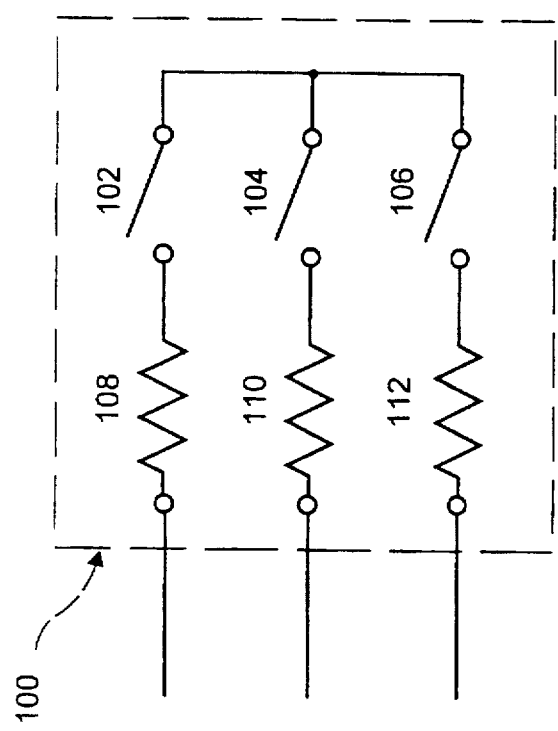
FIG. 5 shows details of a switch arrangement for the embodiment of FIG. 4.

In FIG. 4, switches 44, 45 are illustrated as being idealized switches having no resistance and being associated with discrete resistors. However, preferably, each multi-position switch 44, 45 is implemented as a plurality of electronic switches formed on an integrated circuit, with each switch having a different internal resistance. An example of this arrangement is shown in FIG. 5. According to this embodiment, each switch 44 and corresponding resistors HR and HL are replaced by an IC switch assembly 100 consisting of three switches 102, 104, 106, each having a corresponding internal resistance 108, 110, 112. The resistance 108 corresponds to resistance HR, resistance 110 corresponds to resistance LR, while resistance 112 is very small so that it has virtually no effect on the current. The first, second and third positions described in conjunction with FIG. 3 correspond respectively to switches 102, 104, 106 being closed, respectively. For the fourth position, switches 102, 104, 106 are open.

Although the invention has been described with reference to a preferred embodiment, it is to be understood that this embodiment is merely illustrative of the application of the principles of the invention. Accordingly, the embodiment described in particular should be considered exemplary, not limiting, with respect to the following claims.

We claim:

1. A cochlear implant system comprising:
    a cochlear implant housing;
    a pulse generator generating pulses and disposed in said housing;
    a plurality of electrodes arranged to receive said pulses, said electrodes being inherently charged by electrochemical effects to a parasitic voltage;
    a parasitic voltage circuit for reducing said parasitic voltage by providing a resistive path between said electrodes; and
    a current limiter disposed in said housing for limiting said current through said resistive path to a predetermined maximum, said current limiter including a first impedance selected to provide a first decay at a first time constant and a second impedance selected to provide a second decay at a second time constant faster than said first time constant, said first and second impedance being activated sequentially.

2. The system of claim 1 wherein said electrodes includes a set of intra-cochlear electrodes, and at least one extra cochlear electrode, said resistive path being established between said extra cochlear electrode and one of said intra-cochlear electrodes.

3. The system of claim 1 wherein said pulse generator includes a switch for selectively activating said current limiter prior to said pulses.

4. A cochlear implant system comprising:
    an array of electrodes for stimulating an auditory nerve;
    a pulse generator for generating auditory stimulation pulses;

a plurality of switches for selectively coupling said stimulation pulses electrodes to corresponding pulses; and a current limiting circuit for limiting inrush current between said electrodes, said current limiting circuit including a first resistor selected to provide a first decay for said current and a second resistor selected to provide a second decay, faster then said first, said switches being arranged to activate said current limiting circuit prior to said pulses.

5. The system of claim 4 wherein said switches each have multiple positions.

6. The system of claim 4 wherein said current limiting circuit includes a plurality of resistors selected to limit said current to a preselected maximum level, each resistor being activated when said switches are in a preselected position.

7. The system of claim 4 further comprising control means for activating said first and second resistor sequentially.

8. The system of claim 4 wherein each said switches have a plurality of positions, including a first position coupled to said first resistor, a second position coupled to said second resistor and a third position coupled to said pulse generator.

9. A cochlear implant system comprising:

a cochlear implant housing;

a pulse generator for generating pulses, said pulse generator being disposed in said housing;

a plurality of electrodes arranged to receive said pulses, said electrodes being inherently charged by electrochemical effects to a parasitic voltage between said pulses;

a reducing circuit for reducing said parasitic voltage by producing a resistive path between said electrodes; and a current limiter for limiting a current through said resistive path to a predetermined maximum;

wherein said plurality of electrodes includes a set of intra-cochlear electrodes and an extra cochlear electrode, said resistive path being established between one of said intra-cochlear and said extra cochlear electrode.

* * * * *